(12) United States Patent
Barolat (10) Patent No.: US 8,214,057 B2
(45) Date of Patent: Jul. 3, 2012

(54) SURGICALLY IMPLANTABLE ELECTRODES (75) Inventor: Giancarlo Barolat, Golden, CO (US)

(73) Assignee: Giancarlo Barolat, Denver, CO (US)

( * ) Notice: Subject to any disclaimer, the term of this patent is extended or adjusted under 35 U.S.C. 154(b) by 0 days.

(21) Appl. No.: 12/252,267

(22) Filed: Oct. 15, 2008

(65) Prior Publication Data
US 2009/0099439 A1 Apr. 16, 2009

Related U.S. Application Data (60) Provisional application No. 60/980,402, filed on Oct. 16, 2007.

(51) Int. Cl.
*A61N 1/05* (2006.01)

(52) U.S. Cl. ........................................ 607/118; 607/117

(58) Field of Classification Search .................. 607/117, 607/118, 129, 115; 600/372
See application file for complete search history.

(56) References Cited

U.S. PATENT DOCUMENTS

| | | | |
|---|---|---|---|
| 1,597,061 A | 8/1926 | Cultra | |
| 3,195,540 A | 7/1965 | Waller | |
| 3,646,940 A | 3/1972 | Timm et al. | |
| 3,724,467 A | 4/1973 | Avery et al. | |
| 3,796,221 A | 3/1974 | Hagfors | |
| 3,822,708 A | 7/1974 | Zilber | |
| 3,893,463 A | 7/1975 | Williams | |
| 4,024,875 A | 5/1977 | Putzke | |
| 4,144,889 A | 3/1979 | Tyers et al. | |
| 4,219,027 A | 8/1980 | Frosch et al. | |
| 4,232,679 A | 11/1980 | Schulman | |
| 4,315,503 A | 2/1982 | Ryaby et al. | |
| 4,379,462 A | 4/1983 | Borkan et al. | |
| 4,441,498 A | 4/1984 | Nordling | |
| 4,459,989 A | 7/1984 | Borkan | |
| 4,549,556 A | 10/1985 | Tarjan et al. | |
| 4,581,012 A | 4/1986 | Brown et al. | |
| 4,608,985 A | 9/1986 | Crish et al. | |
| 4,934,368 A | 6/1990 | Lynch | |
| 5,095,905 A | 3/1992 | Klepinski | |
| 5,121,754 A | 6/1992 | Mullett | |
| 5,238,006 A * | 8/1993 | Markowitz | 607/143 |
| 5,282,468 A | 2/1994 | Klepinski | |
| 5,318,572 A | 6/1994 | Helland et al. | |
| 5,324,324 A | 6/1994 | Vachon et al. | |
| 5,330,515 A | 7/1994 | Rutecki et al. | |
| 5,376,103 A | 12/1994 | Anderson et al. | |
| 5,417,719 A | 5/1995 | Hull et al. | |

(Continued)

OTHER PUBLICATIONS

Office Action dated Jan. 28, 2009, received in related matter, U.S. Appl. No. 11/627,337.

(Continued)

*Primary Examiner* — Carl H Layno
*Assistant Examiner* — Luther Behringer
(74) *Attorney, Agent, or Firm* — Haynes and Boone, LLP (57) ABSTRACT Paddle lead electrodes that are capable of performing peripheral nerve stimulation, thereby modulating, controlling and/or reducing neuropathic pain in a patient, that are also surgically implantable, and that will remain fixed in place at the site of implantation when in use are provided. More specifically, one or more embodiments of the electrodes are capable of being surgically implanted underneath a sheath of protective connective tissue that covers electrically excitable tissues and are adapted to electrically stimulate those tissues. Electrodes contemplated by some embodiments are particularly well suited for perineurial implantation. Some embodiments include methods of use associated with the electrodes.

5 Claims, 5 Drawing Sheets

U.S. PATENT DOCUMENTS

| | | | |
|---|---|---|---|
| 5,501,703 A | 3/1996 | Holsheimer et al. | |
| 5,514,175 A | 5/1996 | Kim et al. | |
| 5,522,874 A | 6/1996 | Gates | |
| 5,571,118 A | 11/1996 | Boutos | |
| 5,643,330 A | 7/1997 | Holsheimer et al. | |
| 5,782,901 A * | 7/1998 | Praeger | 607/130 |
| 5,797,923 A | 8/1998 | Aiyar et al. | |
| 5,895,416 A | 4/1999 | Barreras et al. | |
| 5,938,690 A | 8/1999 | Law et al. | |
| 5,948,007 A | 9/1999 | Starkebaum et al. | |
| 5,957,958 A | 9/1999 | Schulman et al. | |
| 6,002,964 A | 12/1999 | Feler et al. | |
| 6,027,456 A | 2/2000 | Feler et al. | |
| 6,104,957 A | 8/2000 | Alo et al. | |
| 6,224,549 B1 | 5/2001 | Drogelen | |
| 6,236,892 B1 * | 5/2001 | Feler | 607/117 |
| 6,246,912 B1 | 6/2001 | Sluijter et al. | |
| 6,309,401 B1 | 10/2001 | Redko et al. | |
| 6,314,325 B1 | 11/2001 | Fitz | |
| 6,330,480 B1 * | 12/2001 | Van der Linden et al. | 607/115 |
| 6,345,199 B1 | 2/2002 | Thong | |
| 6,386,685 B1 | 5/2002 | Sugioka | |
| 6,421,566 B1 | 7/2002 | Holsheimer | |
| 6,438,423 B1 | 8/2002 | Rezai et al. | |
| 6,510,332 B1 | 1/2003 | Greenstein | |
| 6,516,227 B1 | 2/2003 | Meadows et al. | |
| 6,553,263 B1 | 4/2003 | Meadows et al. | |
| 6,609,031 B1 | 8/2003 | Law et al. | |
| 6,675,046 B2 | 1/2004 | Holsheimer | |
| 6,697,676 B2 | 2/2004 | Dahl et al. | |
| 6,735,472 B2 | 5/2004 | Helland | |
| 6,795,737 B2 | 9/2004 | Gielen et al. | |
| 6,885,888 B2 | 4/2005 | Rezai | |
| 6,892,097 B2 | 5/2005 | Holsheimer | |
| 6,895,280 B2 | 5/2005 | Meadows et al. | |
| 6,928,320 B2 | 8/2005 | King | |
| 6,941,171 B2 | 9/2005 | Mann et al. | |
| 6,944,507 B2 | 9/2005 | Froberg et al. | |
| 6,999,819 B2 | 2/2006 | Swoyer et al. | |
| 6,999,820 B2 | 2/2006 | Jordan | |
| 7,006,859 B1 | 2/2006 | Osorio et al. | |
| 7,079,900 B2 | 7/2006 | Greenburg et al. | |
| 7,099,718 B1 | 8/2006 | Thacker et al. | |
| 7,107,097 B2 | 9/2006 | Stern et al. | |
| 7,107,104 B2 | 9/2006 | Keravel et al. | |
| 7,418,298 B2 | 8/2008 | Shiroff et al. | |
| 7,463,932 B2 | 12/2008 | Cawthra et al. | |
| 2002/0111661 A1 | 8/2002 | Cross et al. | |
| 2002/0128700 A1 | 9/2002 | Cross | |
| 2003/0078633 A1 | 4/2003 | Firlik et al. | |
| 2003/0153959 A1 | 8/2003 | Thacker et al. | |
| 2004/0093093 A1 | 5/2004 | Andrews | |
| 2004/0127953 A1 | 7/2004 | Kilgore | |
| 2004/0167584 A1 | 8/2004 | Carroll et al. | |
| 2004/0260310 A1 | 12/2004 | Harris | |
| 2005/0010259 A1 | 1/2005 | Gerber | |
| 2005/0033396 A1 | 2/2005 | Ospyka | |
| 2005/0055065 A1 | 3/2005 | Campbell | |
| 2005/0055779 A1 | 3/2005 | Damewood | |
| 2005/0065394 A1 | 3/2005 | Spiegel | |
| 2005/0070982 A1 | 3/2005 | Heruth et al. | |
| 2005/0107841 A1 | 5/2005 | Meadows et al. | |
| 2005/0119713 A1 | 6/2005 | Whitehurst et al. | |
| 2005/0131506 A1 * | 6/2005 | Rezai et al. | 607/117 |
| 2005/0148149 A1 | 7/2005 | Nabeshima | |
| 2005/0149148 A1 | 7/2005 | King | |
| 2005/0154435 A1 * | 7/2005 | Stern et al. | 607/116 |
| 2005/0182470 A1 | 8/2005 | Cross | |
| 2005/0192644 A1 | 9/2005 | Boveja et al. | |
| 2005/0228451 A1 | 10/2005 | Jaax et al. | |
| 2005/0240242 A1 | 10/2005 | DiLorenzo | |
| 2005/0240243 A1 | 10/2005 | Barolat et al. | |
| 2006/0020317 A1 | 1/2006 | Flach et al. | |
| 2006/0030919 A1 * | 2/2006 | Mrva et al. | 607/118 |
| 2006/0052826 A1 | 3/2006 | Kim et al. | |
| 2006/0052836 A1 | 3/2006 | Kim et al. | |
| 2006/0074450 A1 | 4/2006 | Boveja et al. | |
| 2006/0136008 A1 | 6/2006 | Tadlock | |
| 2006/0178718 A1 | 8/2006 | Jordan | |
| 2006/0265038 A1 | 11/2006 | Hagen et al. | |
| 2008/0051864 A1 | 2/2008 | Callas et al. | |
| 2008/0058876 A1 | 3/2008 | Barolat | |
| 2008/0132970 A1 | 6/2008 | Barolat | |

OTHER PUBLICATIONS

Disorbio et al, "Assessment and Treatment of Chronic Pain"; Practical Pain Management; Mar. 2006; 10 pages.

Swan, "The Nervous System", Jim Swan, revised Oct. 26, 2005, 97 pages.

Amendment and Response to Office Action filed Jul. 29, 2009, in related matter, U.S. Appl. No. 11/627,337.

Lubenow et al, "Advances in Neurostimulation Systems Video Presentation", International Research Foundation for RSD/CRPS, Jul. 16, 2006, 12 pages.

Office Action dated Dec. 11, 2009, issued in U.S. Appl. No. 11/627,337.

* cited by examiner

SURGICALLY IMPLANTABLE ELECTRODES

CROSS REFERENCE TO RELATED APPLICATION

The present application claims the benefit of U.S. Provisional Patent Application No. 60/980,402 filed on Oct. 16, 2007, the entire content of which is incorporated herein by reference in its entirety.

FIELD

The present inventions are generally directed toward an implantable means of modulating or controlling pain in a patient experiencing chronic neuropathic pain or neuropathy. More specifically, embodiments of the present inventions are directed toward a novel, implantable electrode for use in a patient to stimulate peripheral nerves and decrease chronic neuropathic pain, or neuropathy, experienced by that patient, and methods of using the same.

BACKGROUND

The perception of pain is a natural response to tissue injury or trauma. In a normal patient, pain is perceived at the time of injury and is resolved over time as the injury heals. In contrast, neuropathic pain, or peripheral neuropathy, is a disease of the peripheral nerves typified by a chronic or protracted state of pain that continues long after a tissue injury has healed. Like a normal state of pain, peripheral neuropathy is typically caused by acute tissue injury or trauma, however, in the case of neuropathic pain, the nerve fibers themselves are damaged in addition to the tissue, and this damage causes the nerve fibers to function incorrectly. For example, acute damage or trauma to the nerves of the peripheral or central nervous systems can cause individual nerve fibers in those systems to misfire and produce spontaneous signals they would not ordinarily produce (e.g. that are not in response to any normal stimulus) and that the brain and spinal cord do not normally receive. These spontaneous signals are abnormal and, in the case of neuropathy, are perceived by the patient as pain. Because these spontaneous signals typically continue long after the tissue injury or trauma has healed, it is the nervous system itself that is the cause of neuropathic pain, rather than any tissue injury.

Neuropathic pain can be perceived as a steady burning, as a "pins and needles" sensation, as an "electric shock," or as other, similar sensations of pain. In some cases, peripheral neuropathy can result in numbness and abnormal sensations such as dysesthesias (impairment of sensations) and allodynias (exaggerated responses to otherwise non-noxious stimuli), that occur either spontaneously or in reaction to external stimuli. Therefore, neuropathic pain is markedly different in perception and sensation from the ordinary, acute pain that is induced by tissue trauma, such as stubbing a toe or cutting a finger. This difference arises because ordinary pain, or acute pain, which is caused by tissue injury or trauma, is nociceptive in nature (e.g. is caused by a pain stimulus), biologically self-limiting, and serves a protective biological function by acting as a warning of ongoing tissue damage. In contrast, neuropathic pain serves no biological protective function at all; rather than being a symptom of trauma or disease, the pain experienced by the patient is itself the disease. Neuropathic pain is notoriously difficult to treat and tends to respond poorly to standard pain treatments such as analgesics; in some cases even strong opioid or narcotic analgesics such as morphine, codeine and fentanyl, provide limited relief. Neuropathic pain has also been known to worsen over time, rather than improve, making treatment even more challenging for health care providers. Additionally, if chronic neuropathic pain is inadequately treated, other symptoms can develop as a result of the neuropathy apart from those associated with the perception of pain, including chronic anxiety, fear, depression, sleeplessness and impairment of social interaction. In some patients, severe neuropathic pain has even led to physical disability.

The mechanisms of action of neuropathic pain are typically complex and can involve both peripheral and central nervous system pathophysiology. The underlying dysfunction, or cause of the neuropathic state of pain, may involve deafferentation (the elimination or interruption of sensory nerve impulses) within the peripheral nervous system (e.g. neuropathy), deafferentation within the central nervous system (e.g. post-thalamic stroke) or an imbalance between the two systems. An example of neuropathic pain caused by the latter instance, an imbalance between the peripheral and central nervous systems, is the disease state commonly known as "phantom limb syndrome," where a patient has experienced an injury or trauma that has resulted in the loss of a limb, or has had a limb surgically removed. In this case the damage caused to the nerves that originally served the missing limb causes those nerves to malfunction or misfire as described above, which in turn causes the patient's brain to perceive pain in a limb that is no longer present.

Peripheral nerve stimulation ("PNS") was developed as a method for managing chronic or protracted pain in the extremities and has been used as a treatment for neuropathic pain since 1965. PNS uses artificial means, such as electrical impulses, to stimulate the nerves involved in the generation of neuropathic pain, which can include both the nerves involved in the nociceptive pain response and the nerves involved in non-pain, sensory responses (e.g. touch) at the location of the neuropathy, and has been found to reduce the symptoms of neuropathic pain perceived by the patient, sometimes significantly. Several theories as to how and why PNS causes relief from neuropathic pain in some individuals exist, with the generally accepted theory being that, by artificially stimulating the damaged or injured neurons or nerve fibers that cause neuropathic pain, the damaged neurons become desensitized and the pain signals that are sent by those neurons become blocked or down-regulated. The artificial stimulation employed in PNS can range greatly, from large artificial stimuli to small stimuli, but will most typically be used in a range that stimulates the neuropathic pain-causing neurons at a level that is below their minimum threshold firing value. This is done by applying an electrically stimulating signal to an individual nerve or to a bundle of nerve fibers at a level that is above their biological resting potential value, but that is not high enough to trigger depolarization and neuronal firing, in an attempt to decrease the firing sensitivity of those nerves, or to desensitize them to all stimuli so that they transmit fewer signals. For example, the use of PNS to artificially stimulate large, myelinated touch and pressure responsive nerve fibers is theorized to prevent the perception of neuropathic pain generated by those neurons by interfering with their pain signal transmissions and causing those nerve fibers to send non-painful "touch" signals to the brain in their place. While this does not remove the abnormal sensation altogether, it does serve to remove the pain.

PNS is typically performed by placing electrodes along the course of the nerves that are generating neuropathic pain and then using those electrodes to artificially stimulate the neuropathic pain-causing nerves in order to attenuate or control the transmission of pain signals generated. Several devices have been created to perform this task that employ these types of electrodes and they are an extremely safe, efficient, and effective way to ameliorate a variety of severe neuropathic pain conditions. The electrical current generated by the electrodes along the course of the neuropathic nerves effectively tricks the brain into attenuating the painful signals that are being spontaneously generated by the damaged neurons, which causes relief from the neuropathic pain. As a result, most patients are able to reduce or discontinue pain medications after having received PNS. Once the electrodes are put in place, they are used to administer a weak electrical current to the nerve or nerves of interest. In practice, this is typically performed as a two-step process. First, a temporary or trial electrode is put in place along the neuropathic pain-generating nerves and left for a brief period of time so that the patient or health care provider can perform one or more test runs to determine whether PNS will be effective for that patient. The temporary electrode is connected to a power supply outside of the patient that may be controlled by the patient or the health care provider, as appropriate, while PNS is administered to that patient on a trial basis. In the event that PNS is not helpful to the patient, the temporary electrode is removed and the treatment discontinued. If, however, it is found that PNS is providing the patient with relief from neuropathic pain, the temporary electrode is replaced with a permanent electrode that is connected to a power source that is typically surgically implanted inside of the patient, such as a battery pack similar to a pacemaker battery. Once the permanent electrode is in place, the patient may resume the activities of daily living.

Several types of electrodes have been developed for use in performing PNS. Some perform PNS by passing an electric current, and thus providing neurostimulation, through the skin. This form of PNS is called transcutaneous electronic nerve stimulation ("TENS") and is typically accomplished by placing small electrodes topically along the path of the neuropathic pain-generating nerves, on the skin of the patient. TENS therefore has the obvious benefits of being noninvasive and readily adjustable in that the electrodes may be moved, replaced, and relocated along the skin of the patient quickly and easily. In spite of these benefits, however, many patients that have been treated with TENS experience an inadequate or minimal amount of pain relief or worse, experience no pain relief at all. Additionally, even though the electrodes themselves may be small in size and moved with relative ease, many of the accompanying devices necessary to administer TENS to patients are bulky, cumbersome, and non-portable, making TENS impractical for use in ordinary life. Further, because the electrodes are placed topically, the use of TENS precludes contact with water during treatment, thereby preventing patients from enjoying many aspects of normal, daily life without experiencing neuropathic pain.

Other treatment methods using PNS accomplish the desired neurostimulation by surgically implanting electrodes directly to and along the patient's spinal cord. This form of PNS is called spinal cord stimulation ("SCS") and it typically uses a small lead wire as the electrode, which is connected to a power source and surgically implanted to the desired location along the spinal cord. While this procedure has been shown to be medically efficacious in some patients in the relief or reduction in the pain experienced by peripheral neuropathy, it suffers from a unique disadvantage in that several patients question the need to have a spinal procedure performed in order to control limb pain and therefore opt not to receive this form of treatment. An additional, more troubling disadvantage to SCS is that the use of electrodes along the spine and/or spinal nerves of a patient can result in broad electrical coverage regardless of the amount of electrical current delivered, which can result in several nerves being stimulated beyond those causing the neuropathic pain. As may be appreciated, this may induce abnormal sensations at bodily locations that are not damaged or that are otherwise non-painful, because other spinal nerves apart from those generating the neuropathic pain are being stimulated. Because of this, it is often necessary for the health care provider to decrease the amount of electrical current delivered to the spine during SCS in order to minimize the perception of abnormal sensations in non-affected areas. The unfortunate effect of this is that the decreased electrical current also limits the efficacy of SCS, causing the patient to experience limited pain relief. A further disadvantage to SCS is the surgical procedure that is required to accurately place the wire electrodes along the spine. When performing this procedure, it is necessary for the health care provider to accurately place the electrodes so that they stimulate the nerves generating the neuropathic pain, but they must also be properly anchored so that they remain in place after implantation. The disadvantage arises because the techniques traditionally used to anchor the wire electrodes used in SCS in place are imprecise and the electrodes have a tendency to migrate away from their point of surgical implantation in response to minimal pulling forces, such as normal bodily movement, which can lead to several problems with continued pain modulation and can cause electrical stimulation in non-desired areas and of non-desired tissues.

Nothing herein is to be construed as an admission that the present invention is not entitled to antedate a patent, publication or invention by another by virtue of prior invention.

SUMMARY

It would be advantageous to provide an electrode that is capable of performing PNS, thereby modulating, controlling and/or reducing neuropathic pain in a patient, that is also surgically implantable, thereby allowing the patient to participate in normal daily activities, and that will remain fixed in place at the site of implantation while the patient moves normally. Various embodiments of the present inventions address the shortcomings of the known processes and devices. It is to be understood that the present inventions include a variety of different versions or embodiments, and this Summary is not meant to be limiting or all-inclusive. This Summary provides some general descriptions of some of the embodiments, but may also include some more specific descriptions of certain embodiments.

The present inventions provide for paddle lead electrodes that are capable of being surgically implanted underneath any of the plurality of sheaths of protective connective tissues that cover electrically excitable tissue in a patient, and that are capable of directly stimulating those electrically excitable tissues upon implantation. The present inventions also include methods of using and methods of surgically implanting such electrodes. Although well suited for use in human patients, and although much of the discussion of the present inventions is directed toward their use in humans, advantages offered by the present inventions may be realized in the veterinary and scientific fields for the benefit and study of all types of animals and biological systems. Additionally, although the electrodes of the present inventions are particularly well-suited for implantation under the perineurium, and although much of the discussion of the present inventions is directed toward their use in perineurial applications, advantages offered by embodiments of the present inventions may also be realized by implantation under other protective connective tissues, including without limitation the epineurium, the endoneurium, serous membranes, adventitia, the pericardium, the perimysium, and similar protective connective tissues.

In vertebrates, a major structure making up the central nervous system is the spinal cord, which is encased within, and protected by, the spine. The spinal nerves, as part of the peripheral nervous system, serve to connect the central nervous system to the body's sensory receptors, muscles, glands and other components of the peripheral nervous system. Each spinal nerve therefore has a first point of attachment to the spinal cord itself, and at least one, and typically several, second points of attachment to one or more target tissues. In humans, there are thirty-one bilaterally-paired spinal nerves that run the length of the vertebral backbone. Each spinal nerve is comprised of numerous individual neurons, or nerve fibers, that are each individually encased within a sheath of protective connective tissue called the endoneurium, and each of which innervates a target tissue, thereby performing a specific function. Within a single spinal nerve, groups of these individual fibers are arranged into bundles called fascicles, and each fascicle is encased by a sheath of protective connective tissue called the perineurium. There are typically several fascicles in a single spinal nerve, which are bundled together, together with blood vessels and other supporting tissues, and encased by a sheath of connective tissue called the epineurium to form the spinal nerve. The perineurium is therefore one of the supporting structures of the vertebrate peripheral nerve trunks, consisting of layers of flattened cells and collagenous connective tissue which surrounds a fascicle. The perineurium itself is not electrically active and is thus incapable of conducting nerve impulses; it functions as a protective layer for the neural tissues it encases and forms a major barrier to diffusion within a spinal nerve.

In accordance with at least one embodiment of at least one of the present inventions, an implantable surgical electrode is provided that comprises a forward portion located at a first end of the electrode, a back portion located at a second end of the electrode, a plurality of electrical contacts that are disposed within the forward portion in a position that is substantially toward a ventral side of the electrode, a plurality of contact wires, and a lead or cable extending from a dorsal surface of the electrode that is located between the forward portion and the back portion. For one or more embodiments of one or more of the present inventions, the contact wires are preferably fixed to the electrical contacts at a first end and extend from the electrical contacts through the forward portion, and at least partially into the lead.

In accordance with one or more embodiments of one or more of the present inventions, an implantable surgical electrode for electrically stimulating tissues in a patient is provided. The electrode comprises a forward portion located at a first end of the electrode, a back portion located at a second end of the electrode, a plurality of electrical contacts disposed at fixed locations within the forward portion, a plurality of contact wires, equal in number to the electrical contacts, disposed in fixed locations within the forward portion, and a lead extending from a lead connection located on a dorsal surface of the electrode between the forward portion and the back portion. In at least one embodiment of at least one invention, the contact wires are fixed to the electrical contacts at a first end and extend from the electrical contacts through the forward portion and through the lead connection into the lead, and further extend through the lead to a power source. In at least one embodiment of at least one invention the electrode is about 4 cm in length, with the forward portion comprising approximately three-quarters, or approximately 3 cm, of that length, and the back portion comprising approximately one-quarter, or approximately 1 cm, of the remaining length. Additionally, the electrical contacts are disposed within the forward portion in a position that is substantially toward a ventral side of the electrode.

In accordance with still other aspects of the present inventions, a method of surgically implanting an electrode in a patient is presented. In at least one embodiment of at least one of the present inventions, the method comprises first locating a first tissue having a longitudinal axis that is capable of responding to electrical stimulation and that is at least partially enclosed by connective tissue, and creating an opening in the connective tissue that is transverse to the longitudinal axis of the first tissue. Then, once the opening is created, retracting at least a portion of the connective tissue at the opening, providing an electrode having a forward portion, a back portion and a lead located on a dorsal surface of the electrode between the forward portion and the back portion, and positioning the electrode over the opening. Once the electrode is properly positioned, the method further comprises inserting the forward portion of the electrode into the opening and under the connective tissue in a first direction along the longitudinal axis of the first tissue, and then inserting the back portion into the opening and under the connective tissue in a second direction along the longitudinal axis of the first tissue while retaining at least a portion of the lead outside of the opening. Once these tasks are completed, the method is concluded by closing the opening on either side of the lead.

As used herein, "electrode" means a structure that includes an electrical conductor that is used to make contact with and/or electrically stimulate at least one tissue of a patient. U.S. Patent Application Publication No. 2006/0136008 is incorporated herein by reference. Though the description of the inventions includes descriptions of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter.

Various embodiments of the present inventions are set forth in the attached figures and in the detailed description of the inventions as provided herein and as embodied by the claims. It should be understood, however, that this Summary does not contain all of the aspects and embodiments of the present inventions, is not meant to be limiting or restrictive in any manner, and that the inventions as disclosed herein are and will be understood by those of ordinary skill in the art to encompass obvious improvements and modifications thereto.

Additional advantages of the present inventions will become readily apparent from the following discussion, particularly when taken together with the accompanying drawings.

The drawings are not necessarily to scale and the drawings may include exaggerated features for purposes of clarity.

DETAILED DESCRIPTION

Figure 1:
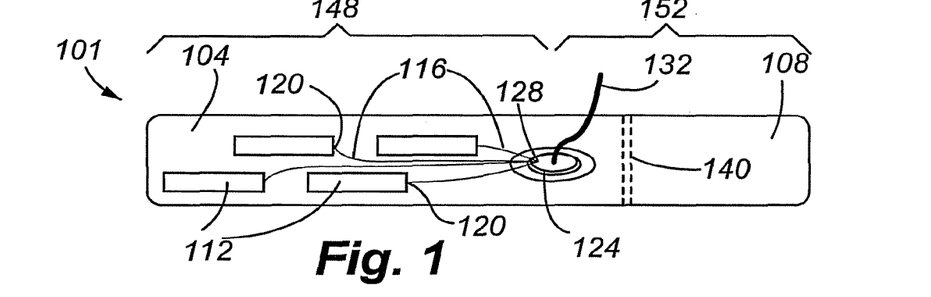
FIG. 1 is a plan view of the dorsal side of an electrode in accordance with at least one embodiment of at least one of the present inventions.
Figure 2:
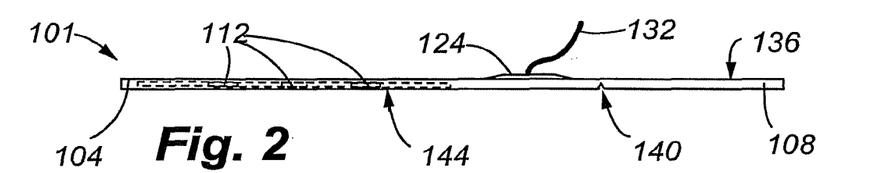
FIG. 2 is a side elevation view of the electrode depicted in FIG. 1.

Referring initially to FIGS. 1 and 2, an electrode 101 in accordance with at least one embodiment of at least one of the present inventions is provided. The electrode 101 preferably includes a forward portion 104, a back portion 108, and at least one, and more preferably, a plurality of electrical contacts 112 arranged in an array and disposed inside of the forward portion 104. The electrode thus comprises a forward portion 104 and back portion 108 that combine to form a paddle. In addition, the electrode 101 preferably further includes at least one, and more preferably a plurality of contact wires 116, each having a first end 120 connected to an electrical contact 112, and each of which extend from the subject contact 112 internally along at least a portion of the length of the forward portion 104 to a lead connection 124 where a second end 128 of the contact wire 116 is bundled together and electrically insulated from other contact wires 116 into a lead 132 or cable that exits the electrode 101 at a location preferably along the electrode's dorsal surface 136 situated between the forward portion 104 and the back portion 108 (see FIG. 2). In at least one embodiment of at least one of the inventions, the contact wires 116 are present in a number equal to the number of electrical contacts 112.

In at least one embodiment of at least one of the inventions, the electrode 101 includes a score, groove or notch 140 on the ventral side 144 of the back portion 108 that preferably spans the width of the electrode 101. The score, groove or notch 140 provides a means of increasing the flexibility of the electrode 101 during surgical implantation, as discussed in further detail below.

In accordance with embodiments of the present inventions, and as generally depicted in the figures, the electrode 101 is substantially rectangular or paddle-like in shape, and the forward portion 104 has smoothed or slightly rounded corners to facilitate surgical implantation. The distal-most end of the forward portion 104 can be configured to any shape suitable for implantation, such as a point, a half circle, and similar shapes, preferably providing a configuration that is sufficiently flat or otherwise shaped so as to not interfere with or damage the tissue encased within the sheath of protective connective tissue, or the connective tissue, upon implantation. In still other embodiments, the forward portion 104 may not only be shaped as described above, but may also taper in thickness to reduce its profile and further facilitate surgical implantation. In one or more embodiments, the shape of the forward portion 104 of the electrode 101 is preferably configured so as to not alter or interfere with the desired array of electrical contacts 112 located inside of the forward portion 104.

The back portion 108 is located at a second end 152 of the electrode 101, opposite from the forward portion 104, and as noted above, in at least one embodiment of at least one of the present inventions, the back portion 108 includes at least one notch 140 on its ventral side 144 that extends to a depth of approximately one-half of the thickness of the electrode 101. In at least one embodiment of at least one of the present inventions, the back portion 108 is substantially rectangular or paddle-like in shape and the distal end of the back portion 108 preferably comprises a shape suitable for implantation, such as that previously described for the forward portion 104. In at least one embodiment, the back portion 108 may be equal in length to, or longer than, the forward portion 104 prior to implantation. Additionally, in one or more embodiments, the back portion 108 may be cut or trimmed to its final size and shape by the surgeon in advance of surgical implantation to sufficiently conform the back portion 108 to the anatomy of the patient. Accordingly, in at least one embodiment the back portion 108 is made of a material that is sufficiently workable so as to facilitate trimming and sizing prior to implantation. In at least one embodiment of the present inventions, the back portion 108 is made of the same material as the forward portion 104 of the electrode 101. Further, in those embodiments of the electrode 101 of the present inventions that include a notch 140, the back portion 108 may be optionally deformed or bent at the notch 140 during implantation along its dorsal surface 136 (see FIG. 4) or along its ventral surface 144 (see FIG. 3), to facilitate implantation.

Figure 14:
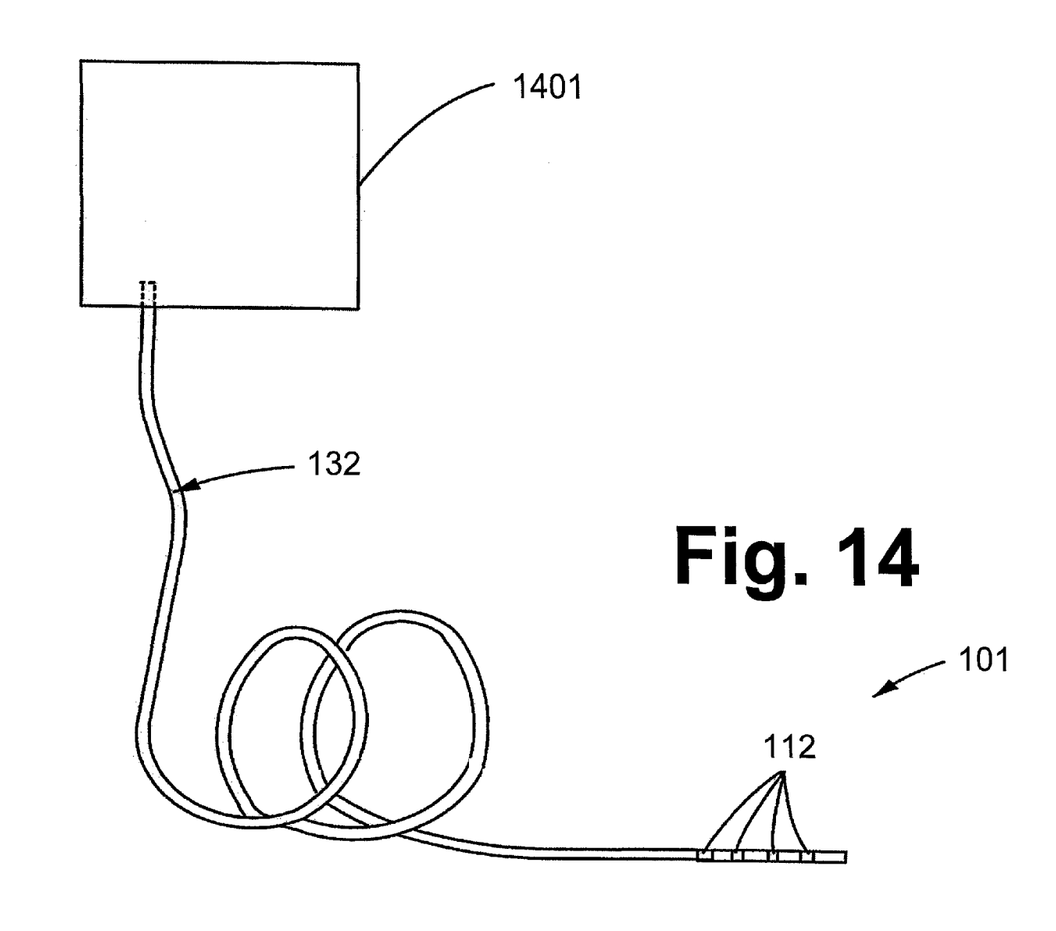
FIG. 14 is a plan view of an electrode, lead and power source in accordance with at least some embodiments of at least one of the present inventions.

The electrical contacts 112 provide a means by which an electrical current is passed from a power source 1401 (see FIG. 14) through the lead 132, contact wires 116, and electrical contacts 112 to the patient's nervous tissue. It is therefore preferable that the electrical contacts 112 be made of a material that conducts and transmits a sufficient amount of electricity to facilitate this purpose. Without wishing to be limited to any one embodiment, the electrical contacts 112 can be made of any material that is medically appropriate to conduct and transmit electricity to a patient's tissues, including, without limitation, a material containing copper, gold, silver, aluminum, platinum, iridium, or a similarly conductive, hard, non-corrosive metal. Alternative materials include conductive polymers and plastics, such as polyacetylene. Tissue compatibility should be checked for all materials implanted. In one aspect of the present inventions, the electrical contacts 112 are sized so as to uniformly fit within the forward portion 104 of the electrode 101, and that size may vary depending upon the number of electrical contacts 112 present in the forward portion 104, as well as with their arrangement. For example, and without wishing to be limited to any embodiment, in the case where the forward portion 104 contains one to seven electrical contacts 112, the contacts 112 may be sized differently than a different electrode 101 having a forward portion 104 with eight or more electrical contacts 112. In the former case, the electrical contacts 112 may be sized larger than the latter case in order to deliver an effective amount of electrical current to the patient's tissues with a fewer number of electrical contacts 112; alternatively, the size of the electrical contacts 112 may not vary so that the electrode 101 with fewer electrical contacts 112 can deliver a smaller amount of current to the patient's tissues than the electrode 101 with more electrical contacts 112. The number of electrical contacts 112 in the forward portion 104 preferably ranges from 1 to 12, more preferably from 4 to 10, and is even more preferably 8. In at least one embodiment of at least one of the present inventions, the electrical contacts 112 are situated within the interior of the forward portion 104 such that they are closer to the ventral surface 144 of the forward portion 104 than the dorsal surface 136 (see FIG. 2). It is preferable that the ventral surface 144 of the electrode 101 make contact with the target tissue. Therefore, the location of the electrical contacts 112 close to the ventral surface 144 of the electrode 101 places them in closer proximity to the tissue of interest, thus facilitating the delivery of electrical current to that tissue.

The contact wires 116 provide the means by which electricity is transmitted from a power source 1401 to the electrical contacts 112. In at least one embodiment of at least one of the present inventions, the contact wires 116 each extend from an electrical contact 112 inside of the forward portion 104 of the electrode 101, through at least a portion of the length of the forward portion 104 to the lead connection 124, and through the lead 132 to a power source. It is also preferable that the contact wires 116 are bundled together and encased within the lead 132 when outside of the electrode 101 (e.g. from the power source to the lead connection 124) and are separated apart from each other inside the forward portion 104 of the electrode 101 so that each individual contact wire 116 may be connected to a single electrical contact 112 at its first end 120. In the present inventions, it is contemplated that the contact wires 116 can be made of any material that is medically appropriate to conduct and transmit electricity from the external power source to the electrical contacts 112 and that is sufficiently flexible so as to resist bending and breaking as the lead 132 and the forward portion 104 bend and flex with the patient's movements. Without wishing to be limited to any one embodiment, it is presently anticipated that the contact wires 116 can be made of platinum, silver, iron, copper, aluminum, gold, tungsten, or another similarly conductive, flexible, non-corrosive metal, as well as conductive polymers and plastics.

The power source 1401 may be a hermetically sealed device containing a power source for generating electrical currents and the computer logic for the electrode 101. The power source 1401 may be surgically implanted in the patient along with the electrode 101, or may optionally be located outside of the patient. The exact configuration and location of the power source will be determined by the surgeon at or prior to the time of implantation of the electrode 101, and may vary from patient to patient. The power source 1401 utilized may be selected from many power sources and/or battery packs typically used to power surgically implantable electrodes and devices, such as pacemaker battery packs, battery packs for implantable cardioverter-defibrillators, or other bio-operable power sources capable of generating sufficient electrical current to stimulate the tissue of interest. An implantable power source is typically spaced apart from the electrode, though that is not required for purposes of the present inventions.

The lead connection 124 is located at a point along the dorsal side 136 of the electrode 101 between the forward portion 104 and the back portion 108 and provides the means by which the contact wires 116 may exit the forward portion 104 and travel, via the lead 132, to a power source 1401. It is therefore preferable that the lead connection 124 and the lead 132 be configured so as to be water-tight, thereby preventing the passage of fluids from the patient or other sources outside of the electrode 101 into the interior of the forward portion 104 and the lead 132, where they may interfere with the ability of the contact wires 116 to properly conduct electricity from the power source to the electrical contacts 112. In at least one embodiment of at least one of the present inventions, the lead 132 is an extension of the material that encases the electrode 101, thereby creating a single sealed environment around the interior of the lead 132 and the forward portion 104 of the electrode 101. Having the lead connection 124 located along the dorsal surface 136 of the electrode 101 between the forward portion 104 and the back portion 108 helps to keep the electrode 101 in place at the surgical site as the patient moves. This is in contrast to locating the lead 132 at other locations along the electrode 101, such as caudally, at one end. When the electrode 101 is implanted inside of a sheath of protective connective tissue it is situated immediately superficial to the electrically excitable tissue of interest. It is thus preferable that the electrode 101 remain in place and not migrate from the surgical site. As will be described in greater detail below, the dorsally-located lead 132 between the forward portion 104 and the back portion 108 helps to distribute external pulling forces exerted on the electrode along the length of the electrode 101 and thus along a line that is largely perpendicular to the direction of pull, thereby helping to keep the electrode 101 in place as the patient moves.

Figure 3:
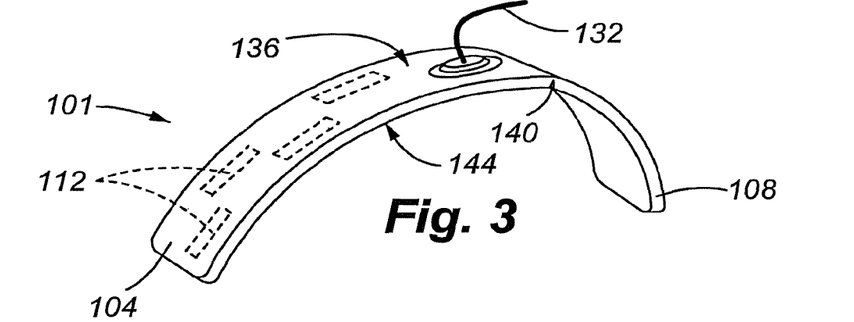
FIG. 3 is a perspective view of the dorsal side of an electrode in accordance with at least one embodiment of at least one of the present inventions, the electrode bent in a curved manner along its ventral side.
Figure 4:
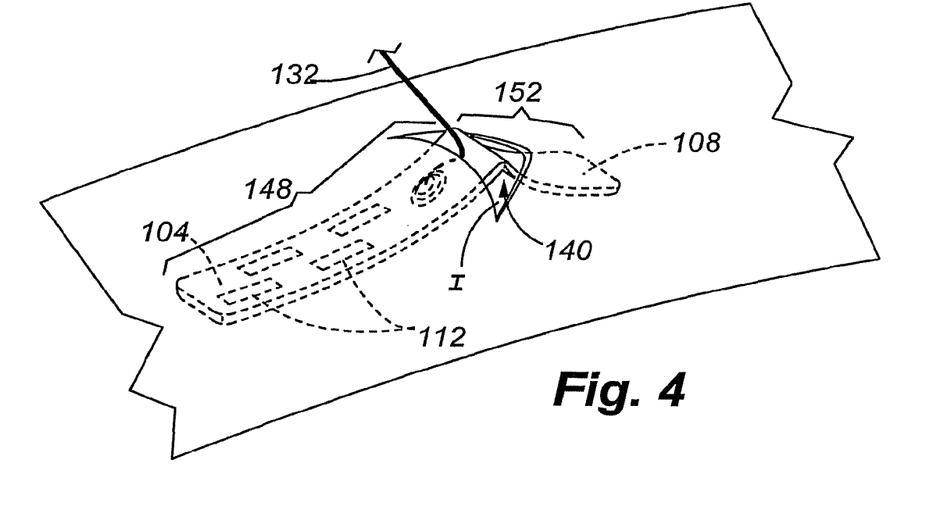
FIG. 4 is a perspective view of the dorsal side of an electrode in accordance with at least some embodiments of at least one of the present inventions, the electrode being placed inside of a surgical incision.

Referring now to FIGS. 3 and 4, an electrode 101 in accordance with at least one embodiment of at least one of the present inventions is presented in a side perspective view. In FIG. 3, the electrode 101 is shown bent in a crescent shape along its ventral surface 144. In FIG. 4, the electrode is shown bent along its dorsal surface 136, in an inverted V-shape, at the notch 140 as it is being inserted into a surgical site, with a slight curvature apparent in both the forward portion 104 and the back portion 108. It is therefore preferable that the electrode 101 be made of a material that is sufficiently flexible so as to allow the electrode 101 to bend and flex both as it is implanted into the patient's body and thereafter in order to conform to the patient's unique anatomy and to help keep the electrode 101 in place at the surgical site as the patient moves. As can be appreciated, a sufficient degree of flexibility will facilitate implantation of the electrode 101, as the electrode 101 will be capable of bending to a substantial degree in order to conform to a surgical site. A sufficient degree of flexibility can also serve to prevent discomfort to the patient and damage to the patient's tissues after the electrode 101 has been implanted, as the electrode 101 will be capable of bending and flexing with the patient's body as the patient undertakes normal daily activities. It is also preferable that the electrode 101 be made of a material that repels water, or that is completely water-tight, so as to prevent the patient's bodily fluids and/or other liquids from entering the electrode 101 and interfering with the transmission of electrical currents to the patient's target tissue. Additionally, it is preferable that the electrode 101 be made of a material that is chemically and electrically inert so as to prevent or impede the dissipation of electrical current away from the contact wires 116 and/or electrical contacts 112 when the electrode 101 is in use and also to allow the electrical current to pass from the electrical contacts 112 to the patient's nervous tissue unimpeded. In at least one embodiment of at least one of the present inventions, the electrode 101 is made of a medical grade, inert, elastomeric polymer such as polytetrafloroethylene, or a silicone elastomer such as Silastic® which is made by and available from The Dow Chemical Company, or any other similar type of flexible material that is suitable for surgical implantation and for purposes of the electrodes 101 of the present inventions.

In FIG. 4, an electrode 101 according to at least some aspects of at least one of the present inventions is shown being placed into a surgical site in a patient. In order to accomplish surgical implantation, an incision I is made in the protective sheath of connective tissue surrounding the tissue of interest, such as the perineurium, thereby exposing the electrically excitable target tissue of interest underneath the connective tissue. By using embodiments of the electrode 101 of the present inventions, the surgical incision I can be quite small, only slightly wider than the total width of the electrode 101 itself, and still be sufficiently sized to allow for proper placement of the electrode 101 along the tissue of interest, such as along the line of the nerves that are associated with neuropathic pain in a patient.

There are several ways in which the electrodes 101 of the present inventions may be placed at a desired location in a patient. In order to place the electrode 101 into the surgical incision I in a manner similar to that depicted in FIG. 4, the electrode 101 may be folded along its ventral surface 144 into an inverted V shape and positioned over the incision I. In those embodiments of the electrodes 101 that include a notch 140 in the ventral surface 144 of the back portion 108, the notch 140 serves to increase the flexibility of the electrode 101, thereby allowing the electrode 101 to be bent at the notch to a greater degree than it otherwise would have been able to in order to facilitate placement into the incision I. By way of example, and without wishing to be limited to any one embodiment, in order to accomplish the surgical placement of the electrode 101 as depicted in FIG. 4, the electrode 101 is bent along its ventral surface 144 at the notch 140 such that it is folded almost completely in half, with the ventral surface 144 of the forward portion 104 and the ventral surface 144 of the back portion 108 brought into contact or very close proximity with each other. Folding the electrode 101 at the notch 140, which is located along the ventral surface 144 of the back portion 108 in the depicted embodiment, results in the first end 148 of the electrode being longer than the second end 152 in the folded configuration. The first end 148 of the electrode 101 is then fed into the incision I and moved underneath the protective connective tissue in the desired direction along the patient's tissue. To aid in proper placement of the first end 148 of the electrode 101, the forward portion 104 of the electrode may be curved or flexed along its dorsal surface 136 as it is fed into the incision I. When the first end 148 of the electrode 101 has been fed into the incision I to the point where the second end 152 is at the opening of the incision I, the second end 152 is fed into the incision I in the opposite direction as the first end 148. It is this point of insertion of the electrode 101 into the incision I that is depicted in FIG. 4. Once both the first end 148 and the second end 152 of the electrode 101 have been inserted into the incision I, the electrode may be moved into the incision I such that the first end 148 and second end 152 spread apart as shown, just underneath the surface of the protective connective tissue. When the electrode 101 is fully inserted into the incision I, the lead 132 will be the only structure of the electrode 101 that extends out of the incision I. Thereafter, the incision I may be sutured closed around the lead 132, securing the electrode 101 in place in the patient. The flexibility of the material of the electrode 101 allows for this type of placement without any loss of function in the electrode 101 and with little to no damage to the underlying tissue.

As can be seen and appreciated from the embodiment depicted in FIG. 4, the lead 132 and the back portion 108 prevent the electrode 101 from moving or migrating in response to pulling forces exerted on the electrode 101 by the patient's surrounding tissues during normal movement. More specifically, in at least one embodiment of at least one of the present inventions, the lead 132 is anchored to the electrode 101 at the lead connection 124, or at a point along the dorsal surface 136 of the electrode 101 that is between its first end 148 and its second end 152, rather than at its caudal end. Because of this, a pulling force exerted on the lead 132 will be distributed and dissipated along the longitudinal plane of the electrode 101, over the forward portion 104 and the back portion 108, in a direction that is largely perpendicular to the direction of the pulling force. This perpendicular distribution of force is in a direction that is away from the direction of the pulling force, thereby preventing the pulling force from moving or removing the electrode 101 from the surgical site. As the patient moves, the surrounding tissues occurring naturally in his or her body will have a tendency to exert pulling forces on the lead 132 from several different directions. As this happens, the electrode 101 of the present inventions resists movement from the surgical site because the lead 132 pulls at a location toward the midline of the electrode 101, rather than at one end. This results in the pulling force being exerted toward the middle of the electrode 101, which would result in movement of the electrode 101 but for the presence of the forward portion 104 and the back portion 108, which resist movement by their location underneath the sheath of protective connective tissue surrounding the tissue of interest. The distribution of a pulling force across the plane of the electrode 101 in a direction that differs from the pulling force helps the electrode 101 resist movement from the surgical site when in use. This is in contrast to other electrodes that may be used for a similar purpose, but that have the lead placed caudally, or at one end of the electrode, as a pulling force exerted along the lead of these electrodes also pulls directly on a terminal end of the electrode. The direction of the pulling force is thus in the same plane as the full length of the electrode, which increases the risk that the direction of pull will cause the electrode to migrate away from the surgical site, or be removed from the site entirely, when in use. The presence of the back portion 108 at the second end 152 of the electrodes 101 of the present inventions thus provides the added length to the electrodes 101 that helps deflect pulling forces across the length of the electrode 101 in a direction that is perpendicular to the original force. The electrodes 101 of the present inventions are thus able to resist migration and movement away from the surgical site as the patient moves because of the presence of the back portion 108.

Figure 5A:
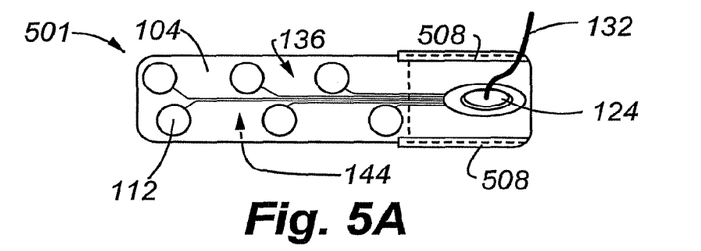
FIG. 5A is a plan view of the dorsal side of an electrode in accordance with at least one embodiment of at least one of the present inventions.
Figure 5B:
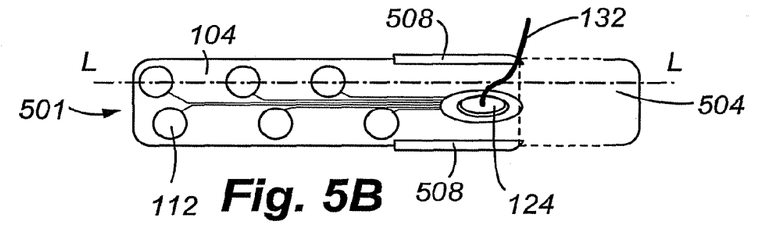
FIG. 5B is a plan view of the dorsal side of the electrode depicted in FIG. 5A, the electrode configured in an extended position.
Figure 6:
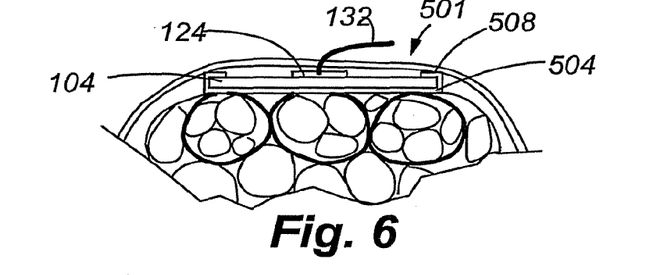
FIG. 6 is a side elevation view of the electrode depicted in FIGS. 5A and 5B that has been surgically implanted along the longitudinal axis of an electrically excitable tissue in a patient.

Referring now to FIGS. 5A, 5B and 6, an electrode 501 according to at least one embodiment of at least one of the present inventions is presented. In the depicted embodiment, the back portion 504 is not included as an integral, planar extension of the forward portion 104, but rather as a telescoping portion that is slid out from around the forward portion 104 after the electrode 501 has been placed in the surgical site. Therefore, the back portion 504 is kept out of the way during insertion of the electrode 501 into the surgical site, and is thereafter extended out from under the forward portion 104 during or after implantation of the forward portion 104, to anchor the electrode 501 in place. in this embodiment, the back portion 504 is a separate sleeve that fits snugly around all or a portion of the forward portion 104 that is configured to slide along the length of the forward portion 104 in one of two directions: away from the first end 148 of the electrode 501 when being extended out to its final, implanted configuration (see FIG. 5B), or toward the first end 148 as it is being retracted. As shown in FIG. 5A, when the back portion 504 is retracted over a portion of the forward portion 104, the length of the electrode 501 is reduced by the length of the back portion 504. This reduction in length facilitates surgical implantation by allowing the electrode 501 to be implanted by sliding it into an incision in a single direction. Although optional, in this embodiment there is less of a need to fold the electrode 501 prior to insertion and thereafter spread the two halves of the electrode 501 once insertion has been achieved, as previously described because the back portion 504 may be fully retracted over a portion of the forward portion 104 during implantation. Preferably, the back portion 504 does not completely encircle or enclose the forward portion 104 of the electrode 501, but is rather shorter in length than the forward portion 104, and comprises a planar portion that spans the width of the electrode's 501 ventral side 144 with two arm portions 508 that extend over the sides of the electrode 501 and at least partially onto its dorsal surface 136 as depicted. As shown in FIG. 5A, when retracted the back portion 504 does not cover any of the electrical contacts 112 contained in the forward portion 104 so as to allow for the intended use of the electrode 501 when the back portion 504 is fully retracted. As can be appreciated, should the back portion 504 cover all or any portion of an electrical contact 112 during use, it may impede or prevent the transmission of electrical impulses from the electrode 501 to the target tissue. By configuring the back portion 504 so that it does not cover any of the electrical contacts 112 even when fully retracted, the electrode 501 may be placed in a patient and put to use without extension of the back portion 504, if so desired, and the surgeon can be assured that the back portion 504 will not interfere with the intended use of the electrode 501. The foregoing notwithstanding, in some embodiments the back portion 504 may be configured to cover some or all of the electrical contacts 112 prior to extension, so as to provide a longer stabilizing portion upon extension. In these embodiments, the back portion 504 may be trimmed to conform to the unique aspects of the patient's anatomy prior to insertion and, in any event, is extended such that it does not cover any electrical contacts 112 during use of the electrode. Furthermore or in the alternative, apertures (not shown) within the back portion 504 can be provided to permit the electrical current to reach the targeted tissue when the back portion 504 is fully retracted.

As can be seen in FIGS. 5A and 6, in at least one embodiment of at least one of the present inventions, the arm portions 508 extend only a short distance across the dorsal surface 136 of the electrode 501. This short distance is still sufficient to hold the back portion 504 to the dorsal surface 144 of the electrode 501 prior to extension and to hold the back portion 504 in place after the electrode 501 has been surgically implanted and the back portion 504 has been at least partially extended. In other embodiments, the arm portions 508 of the back portion 504 extend farther across the dorsal surface 136 of the electrode 501 to any point up to the lead connection 124, thus making the back portion 504 more sleeve-like in appearance. In those embodiments where the arm portions 508 of the back portion 504 extend farther across the dorsal surface 136 of the electrode 501, the back portion 504 has more structure and thus provides for a stronger stabilizing portion of the electrode 501 when extended. In order for the back portion 504 to provide the necessary rigidity to enable it to deflect pulling forces as previously described, in some embodiments the back portion 504 is made of a material that is more rigid than the flexible material of the forward portion 104 of the electrode 501. The use of more rigid material ensures that the back portion 504 will have the structural integrity necessary to remain in place upon extension and to deflect pulling forces as intended. While not wishing to be limited to any one embodiment, the rigid material may include, without limitation, surgical grade plastics, silicone, or rubber.

As shown in FIG. 5B, as the electrode 501 is placed into the surgical site, the back portion 504 is extended away from the forward portion 104 along the longitudinal axis L-L of the electrode 501, bringing the electrode 501 to its full length. This extension may take place by any number of means and by the use of any number of surgical instruments. In at least one embodiment of at least one of the present inventions, the extension may take place by the surgeon using a surgical instrument, such as forceps, wire, a probe, or similar device, to push the arm portions 508 of the back portion 504 away from the forward portion 104 until the back portion 504 is in the desired position. In this embodiment, the back portion 504 may be used to customize the size and length of the electrode 501 both outside of the patient and after placement within the patient. Outside of the patient, the back portion 504 may be trimmed as described above to approximate the size of the surgical site and thus facilitate placement. Once inside the patient, the back portion 504 may be completely extended or extended to a length suitable for the patient's anatomy, depending upon the size and configuration of the surgical site, to further customize the size of the electrode 501. Preferably, when extended to the proper configuration within a patient, the back portion 504 does not cover any portion of the ventral surface 144 of the electrode 501 housing the electrical contacts 112, so as to not prevent the transmission of electricity from an outside source to the patient's tissues.

As can be seen in FIG. 6, the profile of the electrode 501 is not significantly increased with the inclusion of the back portion 504, which is configured to be sufficiently small so as to not increase the thickness of the electrode 501 beyond the anatomical limits of the patient. This facilitates placing the electrode 501 into confined areas, such as underneath the perineurium, as a device that is too thick may cause damage to the patient's tissues during implantation, as well as during normal use. In FIG. 6, the electrode is shown in a side elevation view inside of a surgical site with the back portion 504 not yet extended from the forward portion 104.

Figure 7A:
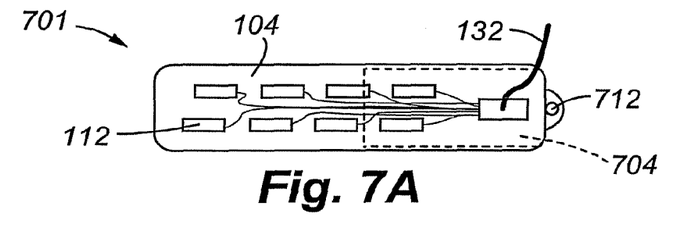
FIG. 7A is a plan view of the dorsal side of an electrode in accordance with at least one embodiment of at least one of the present inventions.
Figure 7B:
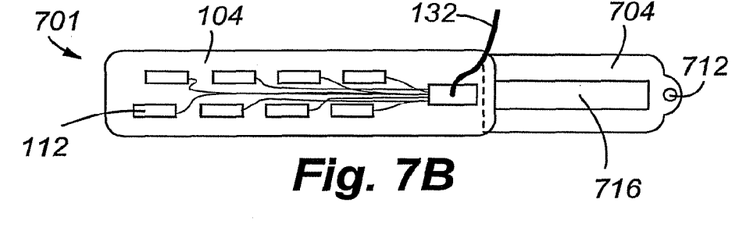
FIG. 7B is a plan view of the dorsal side of the electrode depicted in FIG. 7A, the electrode configured in an extended position.
Figure 8:
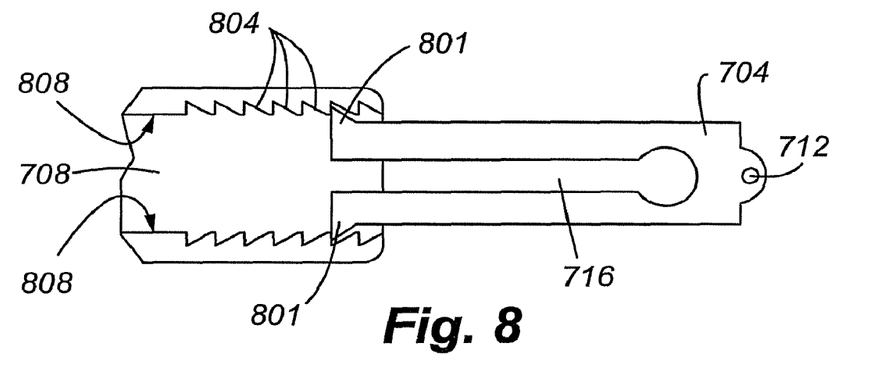
FIG. 8 is an enlarged plan view of the back portion of the electrode depicted in FIGS. 7A and 7B.

Referring now to FIGS. 7A, 7B and 8, an electrode 701 according to at least one embodiment of at least one of the present inventions is presented. In the depicted embodiment, the back portion 704 is not a sleeve-like structure that is slid along the outside of the electrode, but is rather a tab that is extended from the forward portion 104 of the electrode 701 to bring the electrode 701 to full length. In the depicted embodiment, as best seen in FIG. 8, the forward portion 104 of the electrode 701 includes a separate pocket 708 that houses the back portion 704. It is preferable that the pocket 708 be located in the forward portion 104 toward its dorsal surface 136 so as to not create any structures that will interfere with the transfer of electrical impulses from the electrode 701 to the patient. By placing the pocket 708 along the dorsal surface 136, the positioning of the electrical contacts 112 close to the target tissue is maintained.

In the embodiment depicted in FIGS. 7A, 7B and 8, the back portion 704 includes an aperture 712 in the end opposite to the forward portion 104 that may be used to facilitate the extension of the back portion 704 by providing a structure where a surgical instrument may be used to extend the back portion 704. The back portion 704 may optionally include a structural feature that houses the aperture 712, such as a half moon shaped protrusion or similar feature, as shown in FIGS. 7A and 7B. In order to utilize the aperture 712 to extend the back portion 704, a surgical instrument, such as a wire probe or similar instrument with a tip fine enough to fit totally or partially within the aperture 712, may be used to extend the back portion 704 after the electrode 701 has been inserted into the patient, or during insertion. As shown in FIG. 7B, the back portion 704 includes a groove 716 that approximates the width of the lead connection 124. The groove 716 ensures that the back portion 704, when not extended, does not interfere with the contact wires 116 as they are bundled together to move into the lead 132 at the lead connection 124. The groove 716 therefore allows the back portion 704 to extend from the forward portion 104 of the electrode by sliding past the lead connection 124 on both sides. In order for the back portion 704 to provide the necessary rigidity to enable it to deflect pulling forces as previously described, in at least one embodiment of at least one of the present inventions, the back portion 704 is made of a material that is more rigid than the flexible material of the forward portion 104 of the electrode 701. The use of more rigid material ensures that the back portion 704 will have the structural integrity necessary to remain in place upon extension and deflect pulling forces as intended. While not wishing to be limited to any one embodiment, the rigid material may include, without limitation, surgical grade plastics, silicone, or rubber.

Referring now to FIG. 8, an embodiment of the pocket 708 of the forward portion 104 and the back portion 704 is depicted in accordance with at least one embodiment of at least one of the present inventions. In the depicted embodiment, the back portion 704 is held in an extended configuration by a pair of projections 801 that prevent the back portion 704 from backward movement within the pocket 708 by engaging with teeth 804 located along the interior walls 808 of the pocket 708. As the back portion 704 is extended, the projections 801 are moved past the teeth 804 by cooperatively shaped angled surfaces on the projections 801 and teeth 804. The projections 801 are located along a pair of projection arms 812 that are biased to engage the interior walls 808 of the pocket 708. The angled surfaces allow the back portion 704 to move past a single pair of teeth 804 by a slight deflection of the projection arms 812 of the back portion 704. As the projection arms 812 deflect, they move toward each other inside of the pocket 708 in the forward portion 104. Once past the angled face of each tooth 804, the projection arms 812 snap back into their original, undeflected configuration, where the flat surfaces of the teeth 804 are then cooperatively engaged by corresponding flat surfaces of the projections 801, which prevents backward movement of the back portion 704.

Figure 9:
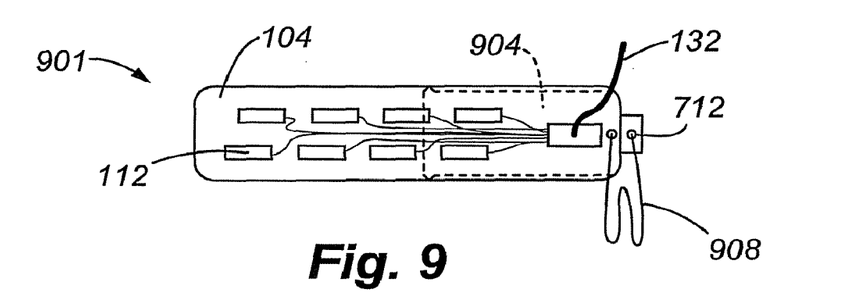
FIG. 9 is a plan view of the dorsal side of an electrode in accordance with at least one embodiment of at least one of the present inventions.
Figure 10:
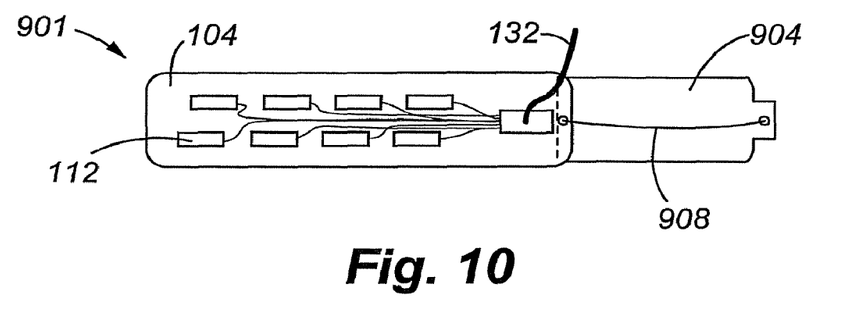
FIG. 10 is a plan view of the dorsal side of the electrode depicted in FIG. 9, the electrode configured in an extended position.

Referring now to FIGS. 9 and 10, an electrode 901 according to at least one embodiment of at least one of the present inventions is shown. In the depicted embodiment, as with the previous embodiment, the back portion 904 is not a sleeve-like structure that is slid along the outside of the electrode 901, but is rather a tab that is extended from the forward portion 104 of the electrode 901 to bring the electrode 901 to full length. The forward portion 104 of the electrode 901 thus similarly includes a separate pocket that houses the back portion 904. It is also preferable that the pocket be located in the forward portion 104 toward its dorsal surface 136 so as to not create any structures that will interfere with the transfer of electrical impulses from the electrode 901 to the patient. It is also intended that this embodiment utilize a way of preventing backward movement, such as that depicted in FIG. 8. Unlike the prior embodiment, however, in this embodiment the back portion 904 is prevented from extending beyond a specified distance by a tether 908 that has one end attached to the forward portion 104 of the electrode 901 and the other end attached to the aperture 712 of the back portion 904. The presence of the tether 908 ensures that the surgeon will not inadvertently remove the back portion 904 from the electrode 901 entirely during extension. Additionally, the tether 908 may be sized to conform to the unique aspects of a patient's anatomy and thus prevent the back portion 904 from being extended to a length that would be harmful to the patient.

As with the previous embodiment, in order for the back portion 904 to provide the necessary rigidity to enable it to deflect pulling forces as previously described, in at least one embodiment of at least one of the present inventions, the back portion 904 is made of a material that is more rigid than the flexible material of the forward portion 104 of the electrode 901. The use of more rigid material ensures that the back portion 904 will have the structural integrity necessary to remain in place upon extension and deflect pulling forces as intended. While not wishing to be limited to any one embodiment, the rigid material may include, without limitation, surgical grade plastics, silicone, or rubber.

For the various embodiments of the electrodes 101, 501, 701, 901 described herein, preferably, the width of the electrodes ranges from approximately 5 to 12 millimeters, more preferably from 8 to 12 millimeters, and more preferably yet, is about 12 millimeters wide. The thickness of the electrodes preferably ranges from approximately 2 to 4 millimeters, and more preferably, is about 3 millimeters thick. The length of the electrodes preferably ranges from about 2 to 6.5 centimeters, more preferably about 3 to 5 centimeters, and more preferably yet, about 4 centimeters long. It is also preferable that the forward portion 104 take up approximately three-quarters, or about 75%, of the length of the electrodes, and the various embodiments of the back portions 108, 504, 704, 904 comprise the balance of the length of the electrodes. As can be seen from the embodiment depicted in FIG. 2, the electrodes are preferably relatively thin in profile, being substantially wider and longer than they are thick. This relatively thin profile facilitates surgical implantation, particularly when the electrodes are placed within a sheath of protective connective tissue covering a tissue of interest. As can be appreciated, this thin profile helps ensure that the electrodes will not damage the tissue of interest during surgical implantation, and also helps ensure that the electrodes do not damage the connective tissue after they have been implanted, such as when the patient moves during normal activity.

In accordance with embodiments of the present inventions, the electrical contacts 112 and contact wires 116 are disposed inside of the forward portion 104 of the electrodes, and are completely encased within the material encasing the electrodes. It is also preferable that the electrical contacts 112 and the contact wires 116 be placed within the forward portion 104 in permanently fixed locations, so as to prevent movement or migration during use. This may be accomplished by any one of several ways and may include, without limitation, setting the contact wires 116 and electrical contacts 112 in their desired locations inside a mold and then pouring or injecting a liquid or molten material over them so as to completely encase them within the forward portion 104 of the electrode. As can be appreciated, by encasing the electrical contacts 112 and the contact wires 116 within the material of the forward portion 104 of the electrodes, the material itself can serve as a water-tight, protective barrier for the electrical contacts 112 and the contact wires 116. A water-tight barrier helps ensure that the electrodes will function properly after they have been implanted into one or more patients, and will not experience any electrical interference from outside liquids and/or a patient's bodily fluids, which are typically water-based and therefore capable of conducting and dissipating, the electrical stimulation delivered to the patient by the electrodes.

The electrical contacts 112 may be arranged in patterns inside of the forward portion 104, with each pattern designed to deliver electrical stimulation to a patient under appropriate physiological conditions. While not wishing to be limited to any particular embodiment, the electrical contacts 112 may be arranged in patterns that include, without limitation, a single electrical contact 112 placed within the forward portion 104, a plurality of electrical contacts 112 arranged in a single line inside of the forward portion 104, a plurality of electrical contacts 112 unevenly spaced within the forward portion 104, a plurality of evenly paired electrical contacts 112 arranged in two substantially parallel lines running the length of the forward portion 104, or a plurality of electrical contacts 112 arranged in a staggered pattern along two parallel lines running the length of the forward portion 104 (see FIG. 1), among others. In some embodiments, the contact wires 116 are placed within the interior of the forward portion 104 so that each connects to a single electrical contact 112 at a first end 120 and then runs at least a portion of the length of the forward portion 104 to the lead connection 124. In those embodiments with two substantially parallel lines of electrical contacts 112, the contact wires 116 are generally centrally disposed in the forward portion 104, and run between the parallel lines generally along the midline of the forward portion 104. It is also an aspect of at least one of the present inventions for the electrical contacts 112 to be configured in any shape that is suitable for the delivery of an electrical current to the tissue of interest. Without wishing to be limited to any one embodiment, and without limitation, the electrical contacts 112 can be shaped as squares, rectangles, circles, or any other shape that will effectively deliver current to the tissue of interest.

In one or more embodiments of one or more of the present inventions, an insulating material is placed inside of the forward portion 104 at a location that is generally between the electrical contacts 112 and the contact wires 116. In this regard, each contact wire 116 passes through the insulating material immediately after its point of attachment to its respective electrical contact 112, and then runs the length of the forward portion 104 toward the lead connection 124 on the opposite side of the insulating material from the electrical contacts 112. In this embodiment, the insulating material is sufficiently flexible so as to not bend or break during normal use of the electrodes and serves as a barrier to the transmission of electricity from the contact wires 116 to the patient's nervous tissue, thereby increasing the accuracy of the placement of the electrical stimulation along the patient's tissues.

All of the dimensions provided herein are for exemplary purposes and are not intended to be limiting. Other dimensions are possible, and such other dimensions are within the scope of the present invention.

Figure 11:
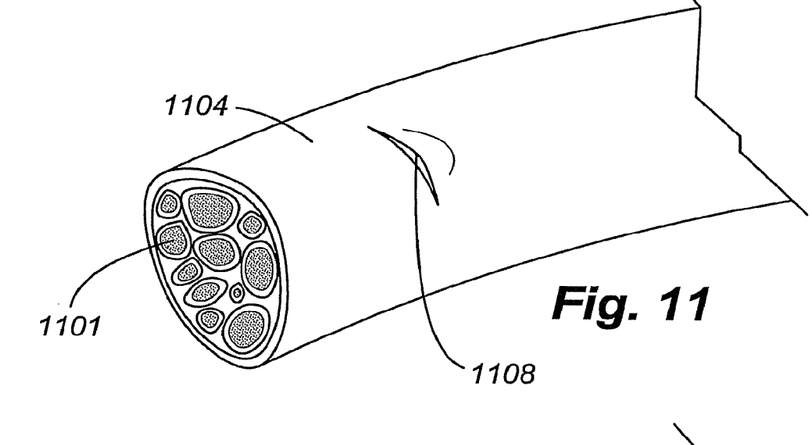
FIG. 11 is a perspective view of a discrete bundle of electrically excitable tissues encased in a sheath of protective connective tissue that has had a transverse opening surgically cut into it in accordance with at least one embodiment of at least one of the present inventions.
Figure 12:
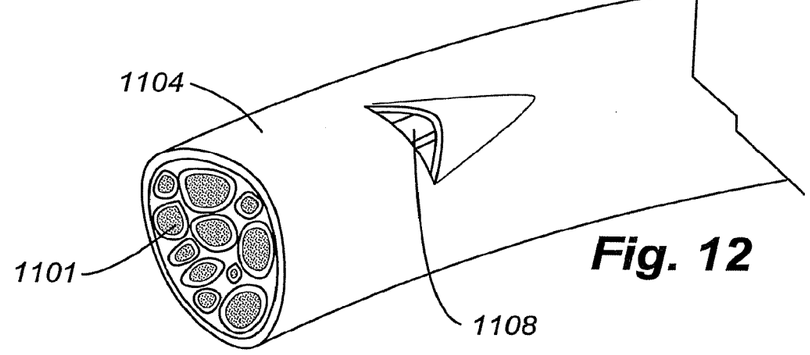
FIG. 12 is a perspective view of the tissues and sheath of connective tissue depicted in FIG. 11, with a portion of the connective tissue retracted away from the transverse opening.
Figure 13:
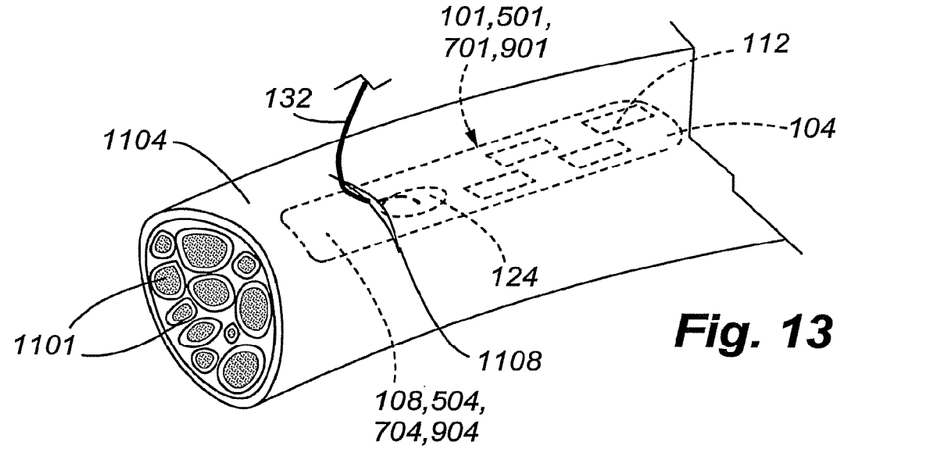
FIG. 13 is a perspective view of the tissues and sheath of connective tissue depicted in FIGS. 11 and 12, with an electrode in accordance with at least one embodiment of at least one of the present inventions surgically implanted underneath the connective tissue.

Referring now to FIGS. 11, 12, and 13, a method of implanting any one of the various embodiments of the electrodes 101, 501, 701, 901 described herein underneath a sheath of protective connective tissue, and thus in contact with an electrically excitable tissue of a patient, according to at least some aspects of at least one of the present inventions is presented. According to the method, a tissue 1101 that is capable of receiving and responding to electrical stimulation and that has a sheath of protective connective tissue 1104, is first surgically located and exposed. In at least one embodiment of at least one of the present inventions, the tissue 1101 is a nerve or group of nerves and the sheath of protective connective tissue 1104 is the perineurium. As seen in FIG. 11, once the tissue 1101 is located, a small, transverse opening 1108 is made in the protective connective tissue 1104, in order to expose the tissue 1101 underneath. The opening 1108 need only be slightly wider than the width of the electrode in order to allow for proper placement of the electrode along the tissue 1101 of interest. In that regard, the method of placing an electrode according to at least one embodiment of at least one of the present inventions only requires a limited exposure of the underlying tissue 1101 in order to place the electrode, since the surgeon only needs to make a small, transverse opening along the protective connective tissue 1104. Thereafter, the protective connective tissue 1104 may be optionally retracted in order to facilitate insertion of the electrode (FIG. 12).

Given that the dimensions of the electrodes of the present inventions are quite small, in that the width of the electrodes preferably ranges from approximately 2 to 4 millimeters thick, the amount of retraction required in advance of insertion is minimal and retraction may not be required in all patients. A decrease in the amount of manipulation of the connective tissue 1104 when performing the methods of the present inventions minimizes the risk of damage to the patient. Once the connective tissue 1104 is sufficiently retracted, the forward portion 104 of the electrode is inserted under the connective tissue 1104 along the long axis of the underlying tissue 1101, which is preferably a nerve. Placing the electrode under the connective tissue 1104 assures that the electrode will be in direct contact with the tissue 48. It is preferable that the electrode is located underneath the connective tissue 1104 in such a way so as to run parallel with the longitudinal axis of the target tissue 1101.

In at least one embodiment of at least one of the present inventions, the forward portion 104 of the electrode is inserted, preferably along the longitudinal axis of the electrically excitable tissue 1101. The forward portion 104 is preferably inserted such that the electrode will provide electrical stimulation to the target tissue 1101 of interest. The back portion 108, 504, 704, 904 is then inserted under the connective tissue 1104 in the opposite direction of the insertion of the forward portion 104. As best seen in FIG. 13, once the forward portion 104 and the back portion have been placed as described, the lead connection 124 will be oriented in the surgical site at the small transverse opening 1108 such that the lead 132 is typically the only portion of the electrode that remains outside of the opening 1108. The small transverse opening 1108 in the connective tissue 1104, is then closed around the lead 132, such as by the use of fine sutures placed on either side of the lead 132. This essentially locks the electrode into position, since the lead 132 prevents it from sliding along its longitudinal axis, and the adhesion of the connective tissue 1104 to the underlying tissue 1101 in areas adjacent to the opening 1108 will keep the electrode from moving from side to side.

Under some circumstances, it may be necessary for the surgeon to reposition the electrode after it has been placed in the patient. In the event that the surgeon determines that the electrode needs to be moved laterally, or sideways along the short axis of the tissue 1101, the transverse opening 1108 need only be elongated in the desired direction. The connective tissue 1104 is then retracted away from the underlying tissue 1101 as previously stated, and the electrode moved. Once the electrode is set in the new position, the opening 1108 is closed around the lead 132 as previously described, thus locking the electrode in place at the new location. In the event that the electrode needs to be repositioned in a longitudinal direction along the length of the target tissue 1101, the connective tissue 1104 can be divided longitudinally, or along the long axis of the tissue 1101, in the desired direction of repositioning. As with repositioning in a transverse direction, the connective tissue 1104 is then retracted and the electrode moved. After repositioning is complete, the additional longitudinal incision is closed around the lead 132 in order to secure the electrode in place.

Embodiments of the present invention may comprise any one or more of the novel features described herein, including in the Detailed Description, and/or shown in the drawings. The claims may include one or more features of any one or more of the embodiments described herein. For example, one or more features of one embodiment may be claimed in combination with one or more features of another embodiment, and no portion of this specification limits such claims.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the inventions has been presented for purposes of illustration and description. The foregoing is not intended to limit the inventions to the form or forms disclosed herein. In the foregoing Detailed Description for example, various features of the inventions are grouped together in one or more embodiments for the purpose of streamlining the disclosure. This method of disclosure is not to be interpreted as reflecting an intention that the claimed inventions require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the inventions.

Moreover though the description of the inventions has included descriptions of one or more embodiments and certain variations and modifications, other variations and modifications are within the scope of the inventions, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An implantable electrode for electrically stimulating tissues, comprising:
   (a) a paddle configured to be implanted subcutaneously comprising:
      (i) a forward portion located along a first end of the paddle, the forward portion including at least one electrical contact disposed within the forward portion substantially toward a ventral surface of the paddle; and
      (ii) a back portion connected to the forward portion and located along a second end of the paddle, wherein the back portion is deformable from the forward portion, and wherein the back portion is devoid of one or more electrical contacts;
   (b) at least one contact wire interconnected at a first end to the at least one electrical contact, the at least one contact wire extending through at least a portion of the forward portion of the paddle, wherein the at least one contact wire is interconnected at a second end to a lead extending from a lead connection located on a dorsal surface of the paddle between the forward portion and the back portion, wherein the lead is adapted to be interconnected to a power source; and
   (c) a notch that extends to a depth of approximately one-half of a thickness of the paddle located on the ventral surface of the paddle that is within and transversely oriented to a longitudinal axis of the paddle;
      wherein the at least one contact wire provides electrical continuity between the at least one electrical contact and the lead; and
      wherein the lead provides electrical continuity between the at least one contact wire and the power source.

2. An implantable electrode for electrically stimulating a tissue, the implantable electrode adapted to be interconnected to a power source using a lead, the implantable electrode comprising:
   (a) a paddle configured to be implanted subcutaneously comprising:
      (i) a forward portion located along a first end of the paddle, the forward portion including at least one electrical contact disposed within the forward portion along a ventral surface of the paddle; and
      (ii) a back portion connected to the forward portion, the back portion being at least one of deformable and extendable from the forward portion, wherein the back portion is devoid of one or more electrical contacts;
   (b) at least one contact wire interconnected to the at least one electrical contact and extending along at least a portion of the forward portion of the paddle, the at least one contact wire providing electrical continuity between the at least one electrical contact and the lead;
   (c) a lead connection located along a dorsal surface of the paddle, wherein the lead connection directionally transitions the at least one contact wire from an orientation substantially planar to the paddle to the lead, the lead situated in an orientation transverse to the dorsal surface of the paddle, and wherein the lead connection is located longitudinally along the dorsal surface between the forward portion and the back portion; and (d) a notch that extends to a depth of approximately one-half of a thickness of the paddle located on the ventral surface of the paddle that is within the paddle and transversely oriented to a longitudinal axis of the paddle.

3. An implantable assembly for treating neuropathy, comprising:
  (a) an implantable electrode configured to be implanted subcutaneously, comprising:
    (i) a forward portion located along a first end of the implantable electrode, the forward portion including a plurality of electrical contacts disposed within the forward portion toward a ventral surface of the implantable electrode; and
    (ii) a back portion connected to the forward portion and located along a second end of the implantable electrode, wherein the back portion is at least one of selectively adjustable and deformable relative to the forward portion, wherein the back portion is devoid of one or more electrical contacts;
    wherein at least one of the forward portion or the back portion comprise a notch extending to a depth of approximately one-half of a thickness of the electrode and located on the ventral surface of the implantable electrode and transversely oriented to a longitudinal axis of the implantable electrode;
  (b) a lead extending from a lead connection located on a dorsal surface of the implantable electrode substantially between the forward portion and the back portion;
  (c) means for providing electrical continuity between the plurality of electrical contacts and the lead; and
  (d) a power source interconnected to the lead at a location spaced apart from the implantable electrode.

4. The assembly of claim 3, wherein the power source is selected from group consisting of a battery pack and a pacemaker battery.

5. The assembly of claim 3, wherein the lead connection directionally transitions the lead from an orientation transverse to the dorsal surface of the implantable electrode to the means for providing electrical continuity located in an orientation substantially planar to the implantable electrode.

\* \* \* \* \*